(12) United States Patent
Saavedra et al.

(10) Patent No.: US 10,436,799 B2
(45) Date of Patent: Oct. 8, 2019

(54) METHODS FOR DIAGNOSING AND TREATING SUBJECTS FOR PULMONARY EXACERBATION

(71) Applicant: National Jewish Health, Denver, CO (US)

(72) Inventors: Milene Saavedra, Denver, CO (US); Vijaya Knight, Centennial, CO (US)

(73) Assignee: National Jewish Health, Denver, CO (US)

( * ) Notice: Subject to any disclaimer, the term of this patent is extended or adjusted under 35 U.S.C. 154(b) by 68 days.

(21) Appl. No.: 15/282,827

(22) Filed: Sep. 30, 2016

(65) Prior Publication Data

US 2017/0102395 A1    Apr. 13, 2017

Related U.S. Application Data

(60) Provisional application No. 62/239,534, filed on Oct. 9, 2015.

(51) Int. Cl.
| | | |
|---|---|---|
| *C12Q 1/6886* | (2018.01) | |
| *G01N 33/68* | (2006.01) | |
| *C12Q 1/6883* | (2018.01) | |
| *G01N 33/49* | (2006.01) | |
| *G01N 33/569* | (2006.01) | |

(52) U.S. Cl.
CPC ....... *G01N 33/6893* (2013.01); *C12Q 1/6883* (2013.01); *G01N 33/4915* (2013.01); *G01N 33/56972* (2013.01); *C12Q 2600/158* (2013.01); *G01N 2333/70535* (2013.01); *G01N 2333/70596* (2013.01); *G01N 2800/382* (2013.01)

(58) Field of Classification Search
CPC .............. G01N 33/6893; G01N 33/80; G01N 33/4915; G01N 33/56972; C12Q 1/6883; C12Q 1/6888
See application file for complete search history.

(56) References Cited

U.S. PATENT DOCUMENTS

| | | | | |
|---|---|---|---|---|
| 8,101,361 B2 * | 1/2012 | Saavedra | ............. | C12Q 1/6883 |
| | | | | 435/6.11 |
| 8,465,923 B2 | 6/2013 | Saavedra et al. | | |
| 9,624,543 B2 * | 4/2017 | Saavedra | ............. | C12Q 1/6883 |
| 2005/0113345 A1 | 5/2005 | Chow et al. | | |
| 2005/0214871 A1 | 9/2005 | Boon et al. | | |
| 2008/0226645 A1 | 9/2008 | O'toole | | |
| 2009/0202514 A1 | 8/2009 | Yoneyama et al. | | |
| 2014/0005099 A1 | 1/2014 | Saavedra et al. | | |
| 2015/0322520 A1 * | 11/2015 | Saavedra | ............... | G16H 50/30 |
| | | | | 514/789 |
| 2019/0128878 A1 | 5/2019 | Saavedra | | |

FOREIGN PATENT DOCUMENTS

| | | |
|---|---|---|
| WO | WO 2004/010139 | 1/2004 |
| WO | WO 2008/023446 | 2/2008 |

OTHER PUBLICATIONS

Saavedra et al. Circulating RNA Transcripts Identify Therapeutic Response in Cystic Fibrosis Lung Disease. Am J Respir Crit Care Med. 178: 929-938 (2008).*
Nick et al. Blood mRNA biomarkers for detection of treatment response in acute pulmonary exacerbations of cystic fibrosis. Thorax. 68: 929-937 (Jun. 2013).*
Carolan et al. "Clinical phenotypes of chronic obstructive pulmonary disease and asthma: recent advances," J. Allergy Clin. Immunol., Mar. 2013, vol. 131, No. 3, pp. 627-634.
Chmiel et al. "The Role of Inflammation in the Pathophysiology of CF Lung Disease," Clinical Reviews in Allergy and Immunology, 2002, vol. 23, pp. 5-27.
Davis et al. "Cystic Fibrosis," American Journal of Respiratory and Critical Care Medicine, 1996, vol. 154, pp. 1229-1256.
Hussein et al. "Neutrophil CD64 expression in inflammatory autoimmune diseases: its value in distinguishing infection from disease flare," Immunological Investigations, 2010, vol. 39, No. 7, pp. 699-712.
Icardi et al. "CD64 Index Provides Simple and Predictive Testing for Detection and Monitoring of Sepsis and Bacterial Infection in Hospital Patients," Journal of Clinical Microbiology, Dec. 2009, vol. 47, No. 12, pp. 3914-3919.
Konstan "Therapies Aimed at Airway Inflammation in Cystic Fibrosis," Clinics in Chest Medicine, 1998, vol. 19, No. 3, pp. 505-513.
McGrath et al. "A large subgroup of mild-to-moderate asthma is persistently noneosinophilic," Am. J. Respir. Crit. Care Med., Mar. 2012, vol. 185, No. 6, pp. 612-619.
Sanders et al. "Return of FEV1 After Pulmonary Exacerbation in Children With Cystic Fibrosis," Pediatric Pulmonology, 2010, vol. 45, pp. 127-134.
Sanders et al. "Failure to Recover to Baseline Pulmonary Function after Cystic Fibrosis Pulmonary Exacerbation," Am. J. Respir. Crit. Care Med., 2010, vol. 182, pp. 627-632.
Sanders et al. "Pulmonary exacerbations are associated with subsequent FEV1 decline in both adults and children with cystic fibrosis," Pediatric Pulmonology, 2011, vol. 46, pp. 393-400.
Singh et al."Altered gene expression in blood and sputum in COPD frequent exacerbators in the ECLIPSE cohort," PLOS One, Sep. 2014, vol. 9, No. 9, e107381, 9 pages.
Waters et al. "Effect of pulmonary exacerbations on long-term lung function decline in cystic fibrosis," Eur. Respir. J., 2012, vol. 40, pp. 61-66.
"measure," The Free Dictionary, 2014, retrieved from www.thefreedictionary.com/measuring, retrieved on Mar. 18, 2014, 3 pages.
"Definition of Detect," The Meriam Webster Dictionary, printed May 20, 2014, [available from: meriam-webster.com/dictionary/detect].
Coleman "Of mouse and man—what is the value of the mouse in predicting gene expression in humans?" Drug Discovery Today, Mar. 2003, vol. 8, No. 6, pp. 233-235.

(Continued)

*Primary Examiner* — Gailene Gabel
(74) *Attorney, Agent, or Firm* — Sheridan Ross P.C.

(57) ABSTRACT

The present invention is related to novel methods for diagnosing and treating acute pulmonary exacerbation in subjects in need thereof.

2 Claims, 8 Drawing Sheets

(56) References Cited

OTHER PUBLICATIONS

Cunningham et al., "Duration of Effect of Intravenous Antibiotics on Spirometry and Sputum Cytokines in Children with Cystic Fibrosis", Pediatric Pulmonology 36:43-48 (2003).
Gray et al. "Sputum and serum calprotectin are useful biomarkers during CF exacerbation," Journal of Cystic Fibrosis, May 2010, vol. 9, No. 3, pp. 193-198.
Gupta "Comparative Gene Expression Profiling of Mediators of Inflammation in COPD versus Asthma Patients: Screening for Potential Pharmacodynamic Response Markers." AAPS PharmSci 3 Meeting Abstracts, 2001, vol. 4, Supplemental #M2311.
Hansel "Oligonucleotide-microarray analysis of peripheral-blood lymphocytes in severe asthma." The Journal of Laboratory and Clinical Medicine, May 2005, pp. 263-274.
Hubeau et al., "Quantitative analysis of inflammatory cells infiltrating the cystic fibrosis airway mucosa", Clin Exp Immunol 2001; 124:69-76.
Kowal et al., "Differential expression of monocyte CD163 in single-and dual-asthmatic responders during allergen-induced bronchoconstriction," Clinical and Experimental Allergy, 2006, vol. 36, No. 12, 1584-1591.
Liou et al. "Sputum Biomarkers and the Prediction of Clinical Outcomes in Patients with Cystic Fibrosis," PLOS ONE, Aug. 2012, vol. 7, No. 8, e42748, 11 pages.
Liu et al. "Comparison of differentially expressed genes in T lymphocytes between human autoimmune disease and murine models of autoimmune disease." Clinical Immunology, Sep. 2004, vol. 112, No. 3, pp. 225-230.
Min et al. "Variability of gene expression profiles in human blood and lymphoblastoid cell lines." BMC Genomics, Feb. 2010, vol. 11, 14 pages.
Moffitt et al. "Inflammatory and immunological biomarkers are not related to survival in adults with Cystic Fibrosis," Journal of Cystic Fibrosis, Jan. 2014, vol. 13, No. 1, pp. 63-68.
Moller et al. "Macrophage serum markers in pneumococcal bacteremia: Prediction of survival by soluble CD163." Critical Care Med, Oct. 2006, vol. 34, No. 10, pp. 2561-2566, (Abstract Only).
Nixon et al., "Circulating Immunoreactive Interleukin-6 in Cystic Fibrosis", Am J Respir Crit Care Med, vol. 157, pp. 1764-1769, 1998.
Ordoñez et al., "Inflammatory and Microbiologic Markers in Induced Sputum after Intravenous Antibiotics in Cystic Fibrosis", American Journal of Respiratory and Critical Care Medicine, vol. 168, 2003, pp. 1471-1475.
Palmer "Cell-type specific gene expression profiles of leukocytes in human peripheral blood" BMC Genomics, May 2006, vol. 7, 15 pages.
Pons et al., "Expression of Toll-like receptor 2 is up-regulated in monocytes from patients with chronic obstructive pulmonary disease," Respiratory Research. 2006, vol. 7, No. 64, pp. 1-9.
Ramilo et al., "Gene expression patterns in blood leukocytes discriminate patients with acute infections", 2007, 109:2066-2077.
Redecke et al., "Cutting Edge: activation of Toll-like receptor 2 induces a Th2 immune response and promotes experimental asthma," The Journal of Immunology, 2004, vol. 172, No. 5, pp. 2739-2743.
Reix et al., "Cytokine pattern in cystic fibrosis patients during antibiotic therapy and gene therapy using adenoviral vector", European Cytokine Network, vol. 13, No. 3, 324-30, Sep. 2002, articles originaux.
Saetre et al. "From wild wolf to domestic dog: gene expression changes in the brain." Molecular Brain Research, Jul. 2004, vol. 126, No. 2, pp. 198-206.
Saiman et al., "Azithromycin in Patients With Cystic Fibrosis Chronically Infected With Pseudomonas aeruginosa," JAMA, 2003, vol. 290(13), pp. 1749-1756.
Shoki et al. "Systematic Review of Blood Biomarkers in Cystic Fibrosis Pulmonary Exacerbations," Chest, Nov. 2013, vol. 144, No. 5, pp. 1659-1670.
Weiss et al., "Soluble CD163: An age-dependent, anti-inflammatory biomarker predicting outcome in sepsis", Crit Care Med 2006 vol. 34, No. 10, pp. 2682-2683.
Wojewodka et al. "Candidate Markers Associated with the Probability of Future Pulmonary Exacerbations in Cystic Fibrosis Patients," PLOS ONE, Feb. 2014, vol. 9, No. 2, e88567, 12 pages.
Wolter et al., "Cytokines and Inflammatory Mediators Do Not Indicate Acute Infection in Cystic Fibrosis", Clinical and Diagnostic Laboratory Immunology, Mar. 1999, p. 260-265.
Woodruff "Genome-wide profiling identifies epithelial cell genes associated with asthma and with treatment response to corticosteroids." PNAS, Oct. 2, 2007, vol. 104, No. 40, pp. 15858-15863.
Wright et al., "Respiratory Epithelial Gene Expression in Patients with Mild and Severe Cystic Fibrosis Lung Disease," American Journal of Respiratory Cell and Molecular Biology, 2006, vol. 35, Iss. 3, pp. 327-336.
Wu et al., "Toll-like Receptor 2 Down-regulation in Established Mouse Allergic Lungs Contributes to Decreased Mycoplasma Clearance", Am J Respir Crit Care Med vol. 1777, pp. 720-729, 2008.

* cited by examiner

METHODS FOR DIAGNOSING AND TREATING SUBJECTS FOR PULMONARY EXACERBATION

CROSS REFERENCE TO RELATED APPLICATIONS

This application claims the benefit of priority under 35 U.S.C. § 119(e) to U.S. Provisional Patent Application Ser. No. 62/239,534, filed Oct. 9, 2015 which is incorporated herein by reference.

FIELD OF THE INVENTION

The field of the present invention involves diagnosing and treating acute pulmonary exacerbation in a subject in need thereof.

BACKGROUND

Cystic fibrosis (CF) impacts 30,000 individuals in the United States and 70,000 individuals worldwide (Patient registry: Annual Data Report. Cystic Fibrosis Foundation 2012; Bethesda, Md.). Mortality from the disease primarily occurs due to progressive respiratory infection and an excessive inflammatory response in the CF lung (Davis P B, Drumm M, Konstan M W. Cystic fibrosis. Am J Respir Crit Care Med 1996; 154:1229-56; Chmiel J F, Berger M, Konstan M W. The role of inflammation in the pathophysiology of CF lung disease. Clin Rev Allergy Immunol 2002; 23:5-27). As the disease progresses, patients experience increasingly frequent pulmonary exacerbations, which in turn increases the risk for subsequent decline (Sanders D B, Hoffman L R, Emerson J, et al. Return of FEV1 after pulmonary exacerbation in children with cystic fibrosis. Pediatr Pulmonol 2010; 45:127-34; Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med 2010; 182:627-3; Waters V, Stanojevic S, Atenafu E G, et al. Effect of pulmonary exacerbations on long-term lung function decline in cystic fibrosis. Eur Respir J 2012; 40:61-6). The number of pulmonary exacerbation episodes suffered in a single year correlates highly with lung function decline in the ensuing three years for both children and adults (Sanders D B, Hoffman L R, Emerson J, et al. Return of FEV1 after pulmonary exacerbation in children with cystic fibrosis. Pediatr Pulmonol 2010; 45:127-34; Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med 2010; 182:627-32; Sanders D B, Bittner R C, Rosenfeld M, Redding G J, Goss C H. Pulmonary exacerbations are associated with subsequent FEV1 decline in both adults and children with cystic fibrosis. Pediatr Pulmonol 2011; 46:393-400). An exceedingly high number of CF patients, 1 in 4, do not recover to baseline Forced Expiratory Volume in 1 second ($FEV_1$) after standard treatment of acute pulmonary exacerbations (APE) (Sanders D B, Hoffman L R, Emerson J, et al. Return of FEV1 after pulmonary exacerbation in children with cystic fibrosis. Pediatr Pulmonol 2010; 45:127-34).

Cystic fibrosis (CF) is the most common lethal inherited disease in the western world. While life expectancies have increased to nearly 40 years, respiratory failure still accounts for >80% of deaths from the disease, usually in young adults in the third or fourth decade of life. The triad of airway obstruction with mucus, chronic endobronchial infection with pathogens such as *Pseudomonas aeruginosa*, and severe airway inflammation, are the major pathogenic factors in CF lung disease (Konstan, 1998, Clin Chest Med 19(3):505-13, vi). Given the shortage of solid organs for transplantation in end stage lung disease, there is a critical need for effective anti-microbial and anti-inflammatory therapies to mitigate progression of disease in this young population.

Progression of CF lung disease is induced by episodic infectious events called acute pulmonary exacerbations (APE). These episodes, which indicate either acquisition of new bacterial infection or a change in the density of previously colonizing bacteria, are poorly defined and difficult to diagnose in the setting of chronic inflammation. Currently, there is no biochemical test to diagnose CF pulmonary exacerbations and no consensus diagnostic criteria for what constitutes an exacerbation. The expression of CD64 on neutrophils is highly specific to acute infection, highlighting its popularity as a sepsis marker (Icardi M, Erickson Y, Kilborn S, et. al. CD64 Index Provides Simple and Predictive Testing for Detection and Monitoring of Sepsis and Bacterial Infection in Hospital Patients. *J. Clin Microbiology.* 2009 December; 47(12):3914-3919). CD64 has also been shown to be capable of detecting acute infection on a background of chronic inflammation (Hussein O A, El-Toukhy M A, El-Rahman H S. Neutrophil CD64 expression in inflammatory autoimmune diseases: its value in distinguishing infection from disease flare. *Immunological investigations.* 2010 39.7:699-712). The inventors have unexpectedly and surprisingly been able to used a flow cytometry based assay to diagnose/predict CF pulmonary exacerbations by quantitative measurement of CD64 expression.

SUMMARY OF THE INVENTION

One embodiment of the invention relates to a method of diagnosing acute pulmonary exacerbation in a subject, the method comprising (a) obtaining a biological sample from the subject; (b) detecting the expression level of CD64 in the biological sample; (c) diagnosing the subject as having acute pulmonary exacerbation when an elevated CD64 expression level from step (b) as compared to a control level is detected.

In one aspect, the method further comprises treating the subject.

Another embodiment of the invention relates to a method of treating a subject at risk for increased pulmonary exacerbation wherein the subject has experienced a previous pulmonary exacerbation, the method comprising (a) obtaining a biological sample from the subject; (b) detecting the expression level of CD64 in the biological sample; (c) identifying the subject as being at risk for increased pulmonary exacerbation when an elevated CD64 expression level from step (b) as compared to a control level is detected; and (d) treating the subject.

Another embodiment of the invention relates to a method for detecting the presence of acute pulmonary exacerbation in a subject in need thereof, the method comprising (a) obtaining a biological sample from the subject; (b) detecting the level of CD64 in the biological sample; (c) detecting the presence of pulmonary exacerbation in the subject when an elevated CD64 expression level from step (b) as compared to a control level is detected.

In one aspect, the method further comprises treating the pulmonary exacerbation in the subject.

In one aspect related to any of the embodiments described herein, the subject has been diagnosed as having a disease selected from the group consisting of cystic fibrosis, asthma, chronic pulmonary obstructive disease, emphysema, interstitial lung disease, bronchitis, acute respiratory distress syndrome, and pneumonia. In one preferred aspect, the subject has been diagnosed as having cystic fibrosis.

In one aspect related to any of the embodiments described herein, the biological sample is whole blood, Peripheral Blood Mononuclear Cells (PBMCs), leuokocytes, neutrophils, monocytes, lymphocytes, basophils, or eosinophils. In one aspect, the biological sample is whole blood.

In one aspect related to any of the embodiments described herein, the expression level of CD64 is detected by quantitative PCR or quantitative flow cytometry (QFCM).

In one aspect related to any of the embodiments described herein the method further comprises measuring the subject's forced expiratory volume (FEV1) and/or C-reactive protein (CPR) levels.

BRIEF DESCRIPTION OF THE DRAWINGS

FIGS. 3A-3D show the gating strategy for whole blood with a representative CF patient sample.

DETAILED DESCRIPTION OF THE INVENTION

Cystic fibrosis (CF) is one of the most common inherited diseases in the western world. Bacterial infectious exacerbations lead to progression of CF lung disease and are challenging to diagnose. CD64, upregulated on neutrophils in response to acute infection, differentiates infection from chronic inflammation. As demonstrated herein, the inventors used quantitative CD64 measurements to diagnose CF pulmonary exacerbations.

The present invention generally relates to novel methods for diagnosing acute pulmonary exacerbation in a subject, and/or categorizing or predicting and/or diagnosing and/or treating subgroups of subjects having an increased risk for increased pulmonary exacerbation and/or disease progression leading to pulmonary decline and in the treatment of a disease that is associated with severe pulmonary exacerbation, such as CF. The inventors have made the surprising and unexpected finding that quantitative analysis of CD64 is a useful tool for diagnosis of acute pulmonary exacerbations in patients in need thereof, such as those with CF. This diagnostic approach thus allows for treatment of APE, including bacterial infectious exacerbations, in these patients.

The invention includes the use of a biomarker whose level correlates with pulmonary exacerbation. The methods of the present invention provide greater sensitivity, specificity and discriminatory capacity than the existing methods for diagnosis of exacerbation. There is currently no consensus guideline nor biomarker validated for diagnosis of exacerbation. Spirometry is a common pulmonary function test for measuring lung function and is frequently utilized as a surrogate marker for diagnosis of exacerbation. Specifically, it is also widely recognized as the standard for assessing pulmonary treatment response, based on whether a patient can return to their baseline values with treatment. When $FEV_1$ measurements are decreased, treatment is initiated. Following two to three weeks of intravenous antibiotic therapy, $FEV_1$ measurements are typically repeated as a quantitative measure of clinical response. Similarly, $FEV_1$ measurements are utilized as the gold standard measurement for treatment response in clinical trials.

The inventors are the first to identify biological pathways underpinning heterogeneity in CF clinical outcomes, in the context of pulmonary exacerbations. Molecular quantification of inflammation has precedence in asthma and chronic obstructive pulmonary disease (COPD) where activation of particular inflammatory pathways corresponds to clinical phenotypes, which differ in terms of underlying inflammation, outcomes, disease progression and response to treatment (Singh D, Fox S M, Tal-Singer R, Bates S, Riley J H, Celli B. Altered gene expression in blood and sputum in COPD frequent exacerbators in the ECLIPSE cohort. PLoS One 2014; 9:e107381; McGrath K W, Icitovic N, Boushey H A, et al. A large subgroup of mild-to-moderate asthma is persistently noneosinophilic. Am J Respir Crit Care Med 2012; 185:612-9; Carolan B J, Sutherland E R. Clinical phenotypes of chronic obstructive pulmonary disease and asthma: recent advances. J Allergy Clin Immunol 2013; 131:627-34; quiz 35). The incorporation of peripheral blood gene signatures adds an additional layer of disease classification beyond the traditional groupings of mild, moderate and severe CF airway disease, based on $FEV_1\%$ predicted. Most strategically, transcriptional classification of disease severity has utility at the time of APE onset, which would allow for health care providers to devise appropriate treatment regimens and follow up for the APE episode and beyond, respectively. The use of transcription profiling of peripheral blood leukocytes led to the identification of CD64. In those studies, the strongest independent predictor of unresolved infection following treatment was circulating CD64 leukocyte expression, the odds of which increased 37% for every 1000 unit increase in CD64 transcript.

The method also includes comparing the level of CD64 from the subject with a baseline level of CD64 established from healthy and/or control subjects and treating the subject aggressively if the subject has or is at risk for increased pulmonary exacerbation. In one aspect, treating the subject aggressively includes but is not limited to one or more of the following treatments: altering the dosing of the drugs or medication (such as administering an antibiotic including administration of the antibiotic by intravenous (IV) administration) the subject is being administered for treating pulmonary exacerbation; altering the quantity of antimicrobial agents the subject is being administered; administering an antimicrobial agent to the subject; increasing the duration of drug(s) and/or antimicrobial agent(s) the subject is being administered.

In one aspect of the embodiments of the invention described herein, the subject has been diagnosed as having a disease selected from cystic fibrosis, asthma, chronic pulmonary obstructive disease, emphysema, interstitial lung disease, bronchitis, acute respiratory distress syndrome, and pneumonia. In a preferred embodiment, the subject has been diagnosed as having cystic fibrosis.

A patient or subject sample can include any bodily fluid or tissue from a patient that may contain the RNA or protein encoded by the genes contemplated here. The term "sample" or "patient sample" or "subject sample" can be used generally to refer to a sample of any type which contains products that are to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

In some aspects, the biological sample from the subject is blood, sputum, bronchoalveolar lavage or urine. In still some aspects the biological sample is whole blood, Peripheral Blood Mononuclear Cells (PBMCs), leuokocytes, neutrophils, monocytes, lymphocytes, basophils, or eosinophils. In a preferred aspect, the sample is whole blood.

A systemic marker of pulmonary exacerbation has many advantages, as blood (such as whole blood) can be obtained from subjects of any age and disease severity, and may reflect the status of exacerbation throughout the lung, rather than one segment. This analysis is sensitive, inexpensive, and obtained from blood and/or tissue that is easily accessible in pediatric and adult populations, and has the potential to be performed in a clinical laboratory.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not and the level at which it expresses. This can include determining whether the gene expression is upregulated or downregulated as compared to a baseline that has been determined from one or more healthy and/or control subjects.

As used herein, reference to a control, means a subject (or population of subjects) who is a relevant control to the subject being evaluated by the methods of the present invention. The control can be matched in one or more characteristics to the subject, including but not limited to gender, age and disease severity. In one aspect, the control can be a healthy subject (i.e. disease free). In another aspect, a baseline level can be established from one or more controls and/or healthy subjects.

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), quantitative PCR and reverse transcriptase-polymerase chain reaction (RT-PCR), and/or followed by quantitative detection of the product by any of a variety of means; extraction of total RNA from the cells, which is then labeled and used to probe cDNAs or oligonucleotides encoding the gene on any of a variety of surfaces; in situ hybridization; flow cytometry and detection of a reporter gene. In a preferred aspect, the expression level of the one or more genes is detected by quantitative PCR.

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, Nature 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

In addition, CD64 levels can be quantitated by Quantitative Flow Cytometry (QFCM), including but not limited to methods such as Quantum MESF beads. QFCM involves the measurement of degrees of fluorescence intensity, usually in terms of Antibody Binding Capacity (ABC) or Molecules of Equivalent Soluble Fluorochrome (MESF). The assay utilizes microspheres that are either pre-labeled with known amounts of fluorochorome or coated with a known amount of capture antibody that must then be stained. These microspheres are used to generate a standard curve from which the relative fluorescence of unknown samples may be determined. While not the equivalent of quantitative chemistry analyses, QFCM has been proven to be a sufficiently robust technique for rapid detection of sepsis (Icardi M, Erickson Y, Kilborn S, et. al. CD64 Index Provides Simple and Predictive Testing for Detection and Monitoring of Sepsis and Bacterial Infection in Hospital Patients. *J. Clin Microbiology.* 2009 December; 47(12):3914-3919), but has not been previously used as a method in the diagnosis and/or detection of pulmonary exacerbation.

In one aspect of the invention, the expression level of CD64 in the subject is at least about 2 fold, at least about 3 fold, at least about 4 fold, at least about 5 fold, at least about 10-fold, at least about 20 fold, at least about 25 fold, at least about 30 fold, at least about 40 fold or at least about 50 fold above the CD64 expression level of the baseline reference/control, such as a CF baseline control. In one aspect, the CD64 expression level in the subject is significantly statistically higher than the CD64 baseline expression level.

Another embodiment of the present invention relates to a kit for detecting the expression of CD64. In one aspect, the kit comprises a detection agent for detecting the expression of CD64. In one aspect, the kit comprises an agent for detecting mRNA expression of CD64. In still another aspect, the kit comprises an agent for detecting CD64 protein expression. In other aspects, the kit comprises an antibody against CD64. In another aspect, the kit comprises microspheres that are either pre-labeled with known amounts of fluorochorome or coated with a known amount of capture antibody.

The following examples are provided for illustrative purposes, and are not intended to limit the scope of the invention as claimed herein. Any variations which occur to the skilled artisan are intended to fall within the scope of the present invention.

EXAMPLE

Methods:
Under IRB approval, blood samples from CF patients (APE) and healthy controls were stained with CD64, CD14 and CD163. CD64 expression on neutrophils was quantitated utilizing Quantum MESF beads.

Materials:
FACSCanto II from BD Biosciences
Quantum MESF FITC bead set from Bangs Laboratories, Inc
CD14 APC and CD64 FITC from Affymetrix eBiosciences
Cytochex Vacutainer tubes from Streck, Inc Instrumentation:
The FACSCanto II linearity was assessed and the FITC PMT was found to be linear down to a channel number of 85 with a $R^2$ of 0.9998.

Fluorochrome and Marker Selection:
CD163 and CD14 were compared for exclusion of monocytes. The stability of CD14 in the presence of heparin made it the marker of choice. PE and FITC-labeled CD64 were analyzed and found to be comparable. FITC was chosen as the more cost-effective reagent.

Anticoagulant:
Heparin, EDTA, Citrate and Cytochex preservative were compared and found to be comparable in marker expression. Expression remained stable in the Cytochex preservative for up to 72 hours post collection.

Sample Processing:
100 mcL of preserved whole blood was added to an antibody cocktail of CD14 and CD64, incubated, lysed and washed according to standard protocols.

Instrument Standardization:
The FACSCanto II was standardized using CS&T and 7 Color beads according to BD protocols.

Sample Analysis:
Quantum MESF FITC beads were run according to the Bangs Laboratories protocol. Samples were run at the same time and the results plotted on the curve.

Results:
For assay optimization, CD163 and CD14 were compared to gate out monocytes. Stability of CD14 in the presence of heparin made it the marker of choice. CD64 expression was comparable for blood collected in heparin, CYTO-CHEX® and citrate tubes. Expression remained stable in the CYTO-CHEX® tubes up to 72 hours following collection.

Figure 1:
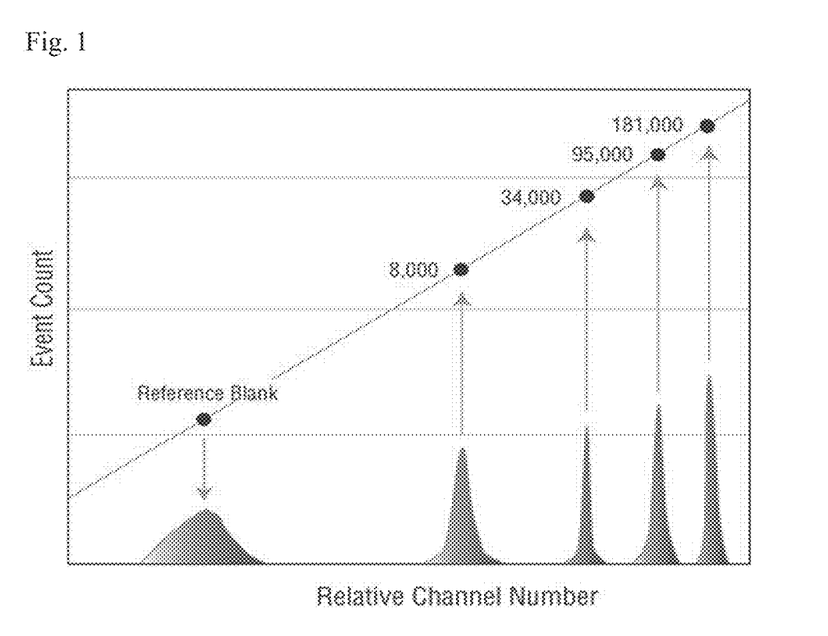
FIG. 1: QFCM Standard Curve. Figure from Bangs Laboratories Inc.
Figure 2:
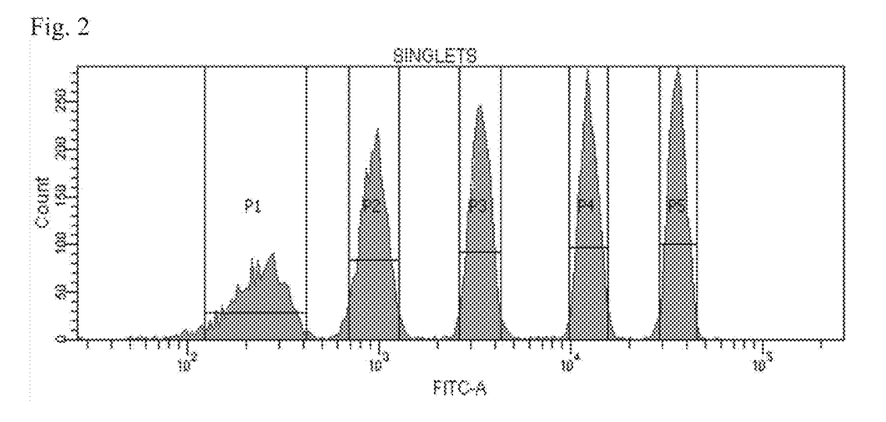
FIG. 2: Gating strategy for MESF beads to generate the standard curve. The peaks show the different fluorescent intensities of the individual bead sets contained in the kit.
Figure 3A:
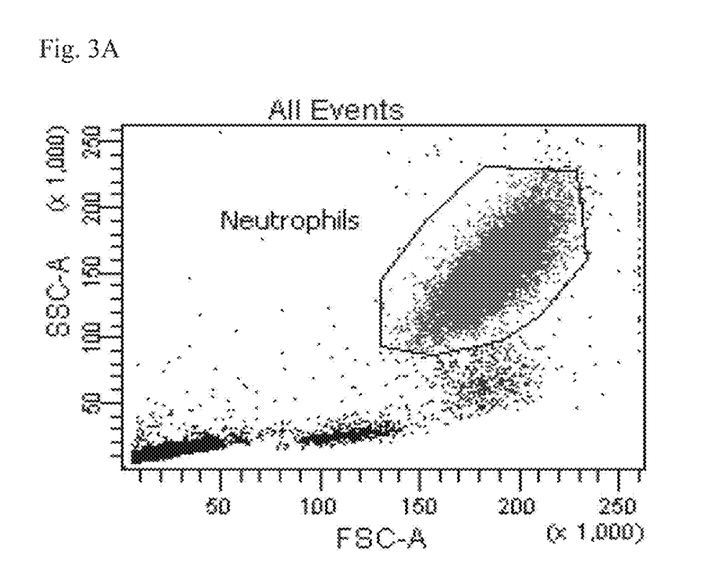
FIG. 3A: Gating on neutrophils using forward and side scatter.
Figure 3B:
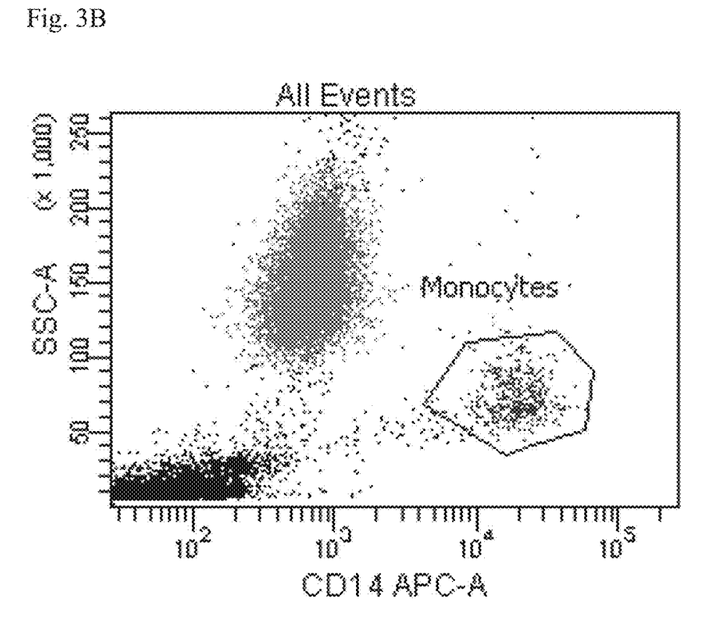
FIG. 3B: CD14 staining to identify and exclude monocytes.
Figure 3C:
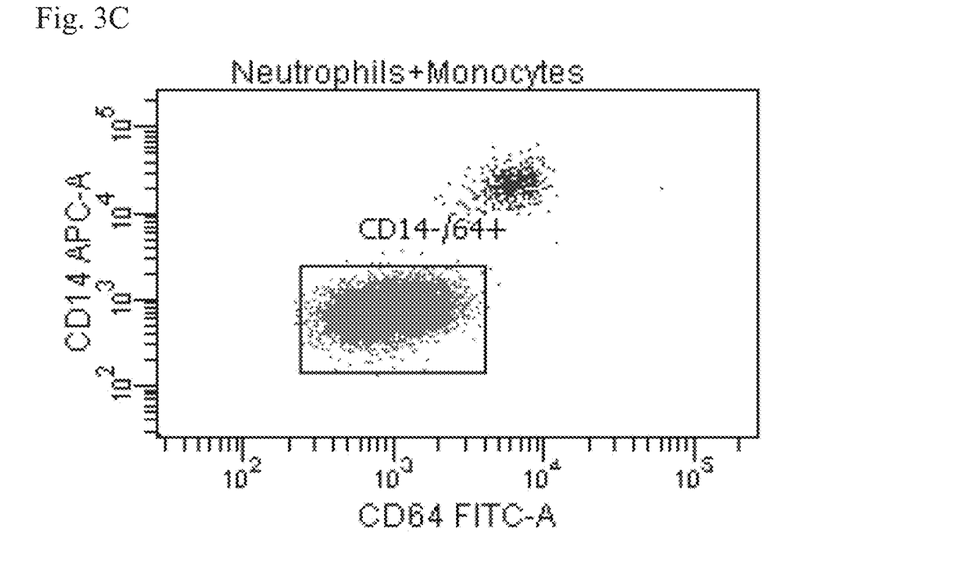
FIG. 3C: Selected population of neutrophils.
Figure 3D:
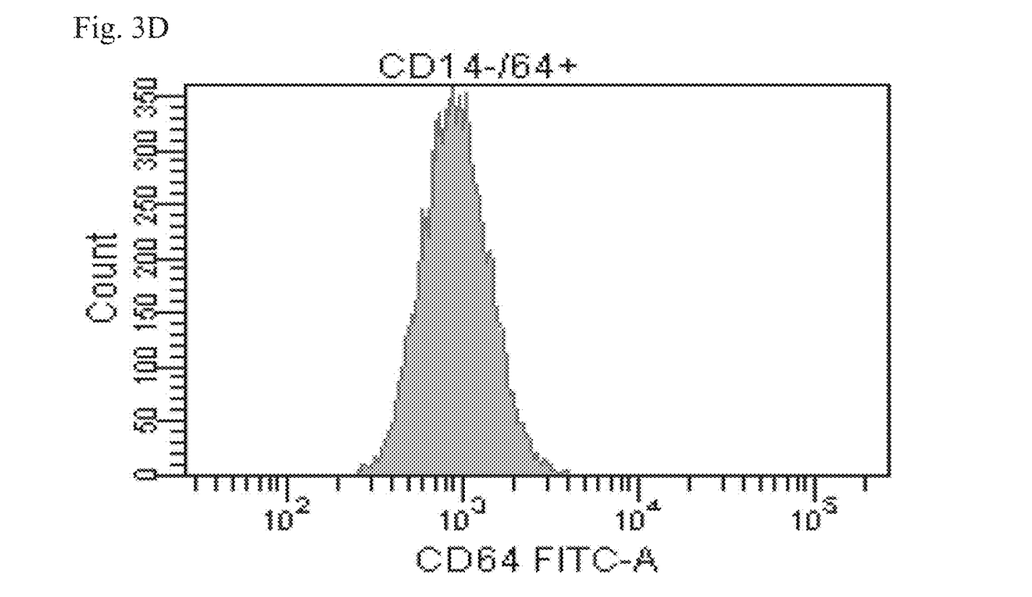
FIG. 3D: Measuring CD64 expression in this population.
Figure 4:
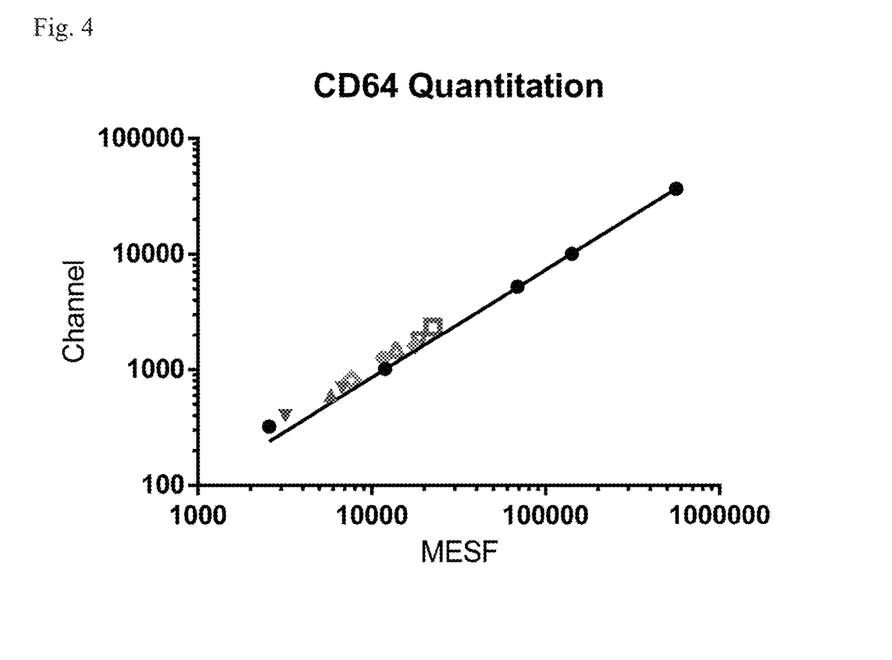
FIG. 4: Resulting standard curve (black line and symbols) with representative patient samples plotted (colored symbols, N=9).
Figure 5:
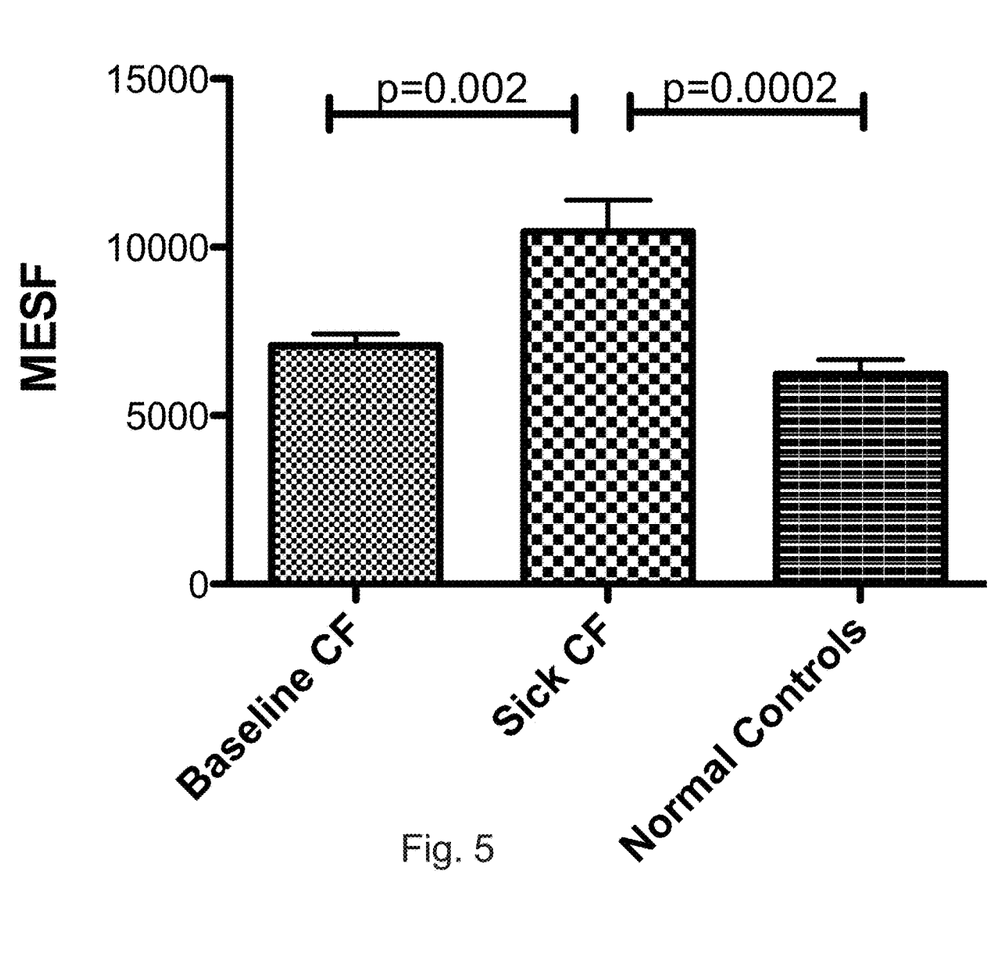
FIG. 5: Comparison of CD64 expression between infected (APE) (N=45), baseline (N=42) and healthy non-CF patients (N=22). Statistical analysis was performed using a two-tailed t-test. Error bars represent one standard deviation of the mean.
Figure 6:
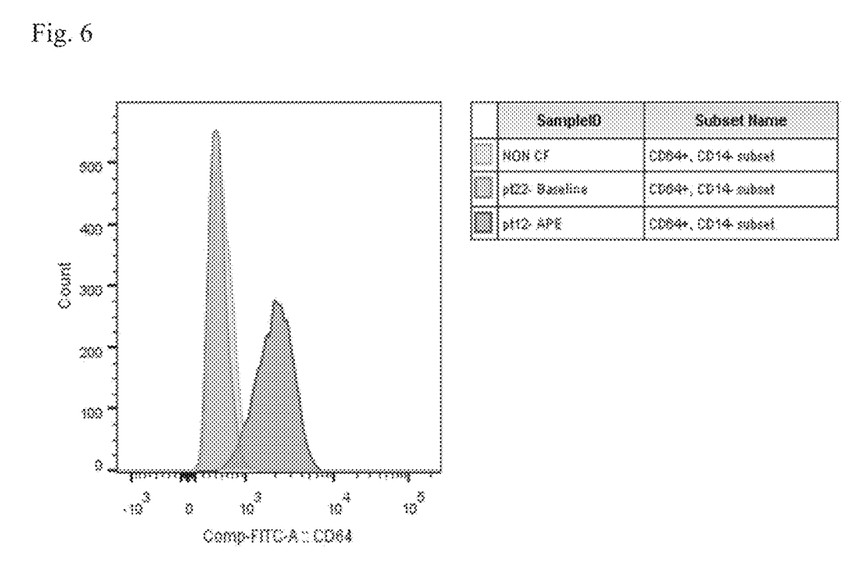
FIG. 6: Histogram comparison of CD64 expression between CF patients during an infection (APE) and baseline as well as non-CF healthy controls.

Eighty-seven unique patient samples were analyzed (acute exacerbations (N=45), baseline health (N=42)) and 22 controls. CD64 was significantly higher at the time of acute exacerbation than at baseline in CF patients (p=0.002) and were significantly higher than values in normal controls (p=0.0002). (FIG. 5).

The results demonstrate that quantitative analysis of CD64 is a useful tool for diagnosis of acute pulmonary exacerbations in CF patients. CD64 is stable for up to 7 days when collected in Cyto-Chex® vacutainers and can be analyzed in 100 mcL of blood. Results can also be obtained within 24-48 hours, making it a rapid tool for the diagnosis of infectious exacerbations in CF patients.

Since only 100 mcL of blood is needed and the results can be obtained within 24-48 hours, quantitative CD64 analysis can be used in the diagnosis of infectious exacerbations.

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:
1. A method of determining and treating a cystic fibrosis (CF) subject for increased risk of acute pulmonary exacerbation (APE), the method comprising:
 a. obtaining and isolating neutrophils from a sample of peripheral blood mononuclear cells (PBMC) from the subject;
 b. detecting the expression level of CD64 in neutrophils of the sample, wherein the expression level of CD64 is detected by quantitative flow cytometry (QFCM);
 c. identifying the subject as being at risk for increased acute pulmonary exacerbation when an elevated CD64 expression level in the neutrophils from step b is measured as compared to a normal non-CF control or control with stable CF or within-subject control before or after treatment; and
 d. administering an effective amount of antibiotic or antimicrobial therapy to treat acute pulmonary exacerbation in the CF subject based on the measured elevated CD64 expression level in the neutrophils of the CF subject identified in step c.
2. The method of claim 1, wherein the subject identified as having an increased risk for pulmonary exacerbation will have an increased risk of morbidity, mortality, and/or an increased risk for exacerbation recurrence.

* * * * *